(12) United States Patent
Drobnik et al.

(10) Patent No.: US 8,454,489 B2
(45) Date of Patent: Jun. 4, 2013

(54) IMPLANT COMPRISING RADIOACTIVE SEEDS

(75) Inventors: Michael W. Drobnik, Downers Grove, IL (US); Christopher D. Drobnik, Wauconda, IL (US)

(73) Assignee: C. R. Bard, Murray Hill, NJ (US)

( * ) Notice: Subject to any disclaimer, the term of this patent is extended or adjusted under 35 U.S.C. 154(b) by 802 days.

(21) Appl. No.: 12/224,638

(22) PCT Filed: Mar. 14, 2007

(86) PCT No.: PCT/US2007/006422
§ 371 (c)(1),
(2), (4) Date: Sep. 2, 2008

(87) PCT Pub. No.: WO2007/106531
PCT Pub. Date: Sep. 20, 2007

(65) Prior Publication Data
US 2009/0131735 A1    May 21, 2009

Related U.S. Application Data

(60) Provisional application No. 60/781,751, filed on Mar. 14, 2006.

(51) Int. Cl.
*A61N 5/00* (2006.01)

(52) U.S. Cl.
USPC .................................. 600/8; 600/3

(58) Field of Classification Search
USPC ........................................................ 600/1–8
See application file for complete search history.

(56) References Cited

U.S. PATENT DOCUMENTS

| 4,754,745 | A |   | 7/1988 | Horowitz |
| 4,946,435 | A | * | 8/1990 | Suthanthiran et al. ............ 600/3 |
| 5,030,195 | A |   | 7/1991 | Nardi |
| 6,248,057 | B1 | * | 6/2001 | Mavity et al. ..................... 600/3 |
| 6,270,472 | B1 | * | 8/2001 | Antaki et al. .................... 604/61 |
| 6,293,899 | B1 | * | 9/2001 | Sioshansi et al. ................. 600/3 |
| 6,482,142 | B1 |   | 11/2002 | Winkler et al. |
| 6,575,887 | B1 | * | 6/2003 | Schrayer .......................... 600/3 |
| 2003/0208096 | A1 |   | 11/2003 | Tam et al. |
| 2006/0173235 | A1 | * | 8/2006 | Lim et al. ......................... 600/6 |

* cited by examiner

*Primary Examiner* — Christine Matthews
*Assistant Examiner* — Carrie R Dorna
(74) *Attorney, Agent, or Firm* — Carmen Patti Law Group, LLC

(57) ABSTRACT

The present disclosure relates to an implant comprising at least two sheets of a biocompatible material, and at least one radioactive seed disposed between said sheets of material. The disclosure also relates to a method for treating a patient, comprising fixing to the tissue of the patient at least one implant comprising at least two sheets of a biocompatible material, and at least one radioactive seed disposed between said sheets of material.

39 Claims, 4 Drawing Sheets

IMPLANT COMPRISING RADIOACTIVE SEEDS

CROSS-REFERENCE TO RELATED APPLICATIONS

This application is a 371 of PCT/US2007/006422, filed Mar. 14, 2007, which claims priority of U.S. Provisional Application 60/781,751, filed Mar. 14, 2006.

BACKGROUND

Bodily cancers are commonly treated using radiation therapy. Radiation therapy employs high energy radiation to kill cancer cells. One type of radiation therapy is brachytherapy, in which a source of radiation is in direct contact with an afflicted tissue. A common brachytherapy treatment, transperineal seed implantation, involves placing radioactive seeds in the prostate gland to kill prostate gland cancer cells. A physician employs tools such as ultrasound, computerized tomography ("CT") scans, and X-ray images in concert with dose-planning computer software programs to evaluate the medical condition of a patient. The physician constructs an optimal treatment plan to evenly distribute radiation throughout the afflicted tissue. Radioactive seeds of discrete radioactive strengths are inserted through multiple implantation needles at positions in the prostate gland corresponding to the treatment plan. Multiple implantation needles are required to insert the radioactive seeds into multiple locations in the afflicted tissue, with each needle containing a specified arrangement of the radioactive seeds.

Although brachytherapy is perhaps most often effected by needle implantation, other implantation methods have also been used. One example is a configuration employing seeds and sutures. To make such a configuration, the physicians have utilized a seed product (e.g., Seed in Carrier, manufactured by Oncura) that consists of seeds disposed within a suture material. The sutures are weaved through a piece of bioabsorbable fabric to yield a planar array of seeds. This array is then used to irradiate a tumor bed, most commonly following a lung resection, by sewing the array to the wall of the tumor bed.

Gross surgical removal of tumorous tissue can leave behind traces of cancerous tissue which can result in mestatasis or recurrence of the tumor. Thus, the site of removal of a tumor is often treated postoperatively in an attempt to destroy any such diseased tissue left behind by the surgery. Conventional techniques for treating the site of surgical removal of a tumor include post-operative administration of radiation, chemotherapy, and/or heat. Another method is disclosed in U.S. Pat. No. 5,030,195, the disclosure of which is incorporated by reference herein. In accordance with that disclosure, seeds can be threaded into a mesh, and the mesh embedded in a nonabsorbable silicone compound. Once the exact location and extent of a tumor is determined, the tumor is removed, and the mesh/silicone material is embedded in a region where residual tumor cells may exist.

Proper seed placement and seed retention at the implantation site strongly influence the success or failure of a brachytherapy procedure. As described above, seed implantation devices may contain a plurality of seeds that may be separated by spacers. Prior implantation devices and methods do not reliably maintain proper seed spacing during and after implantation. Therefore, a device and/or method of reliably maintaining proper seed spacing during and after implantation would be of great benefit to brachytherapy patients.

Loose seeds implanted in the prostate, especially those that are extra-capsular (located outside the capsule of the prostate), may possibly migrate within the patient. Because extra-capsular tissue is less dense than tissue within the capsule of, e.g., the prostate, prior brachytherapy seed implantation devices and methods cannot effectively maintain the location of seeds in the extra-capsular material. These seeds may migrate and fail to provide radiation where needed. Migrating radioactive seeds not only fail to provide needed radiation therapy at the treatment site, but may cause damage to other radiation-sensitive areas of the body. Therefore, a device and/or method of preventing migration of radioactive seeds in tissues and/or fluids of varying densities and consistencies would be of great benefit to brachytherapy patients.

In view of the above, it would be desirable to have an implant, whether standard or custom, that is capable of delivering radiation to a patent in need thereof without the above-mentioned disadvantages.

SUMMARY

According to one aspect of the present disclosure, there is provided an implant comprising at least two sheets of a biocompatible material, and at least one radioactive seed disposed between said sheets of material.

According to another aspect of the present disclosure, there is provided a method for treating a patient, comprising fixing to the tissue of the patient at least one implant comprising at least two sheets of a biocompatible material, and at least one radioactive seed disposed between said sheets of material.

According to yet another aspect of the present disclosure, there is provided a method for treating a patient, comprising surgically excising at least a portion of a tumor from surrounding tissue, and providing at least one implant at the locus of said surrounding tissue, wherein the implant comprises at least two sheets of a biocompatible material, and at least one radioactive seed disposed between said sheets of material.

BRIEF DESCRIPTION OF THE DRAWINGS

The disclosed embodiments can be better understood with reference to the following drawing. The components in the drawing are not necessarily to scale.

DESCRIPTION

Figure 1:
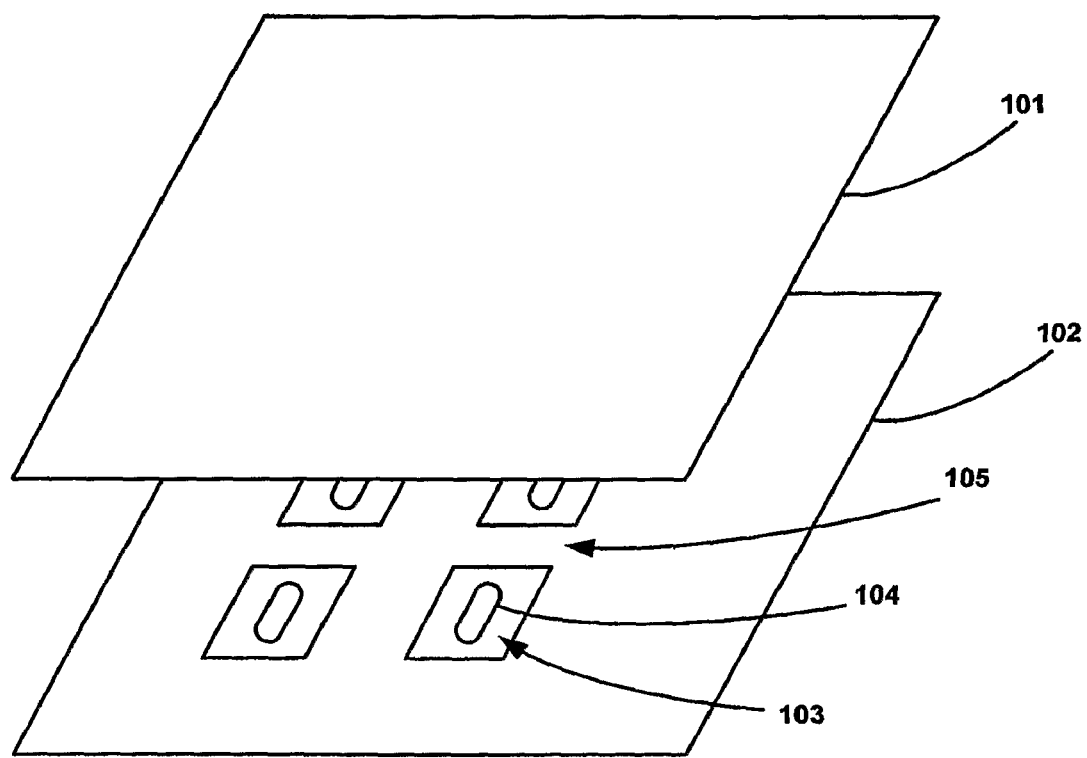
FIG. 1, according to various embodiments, is an illustration of an implant in accordance with the present disclosure.

According to various embodiments, the present disclosure relates to an implant comprising at least one seed in a carrier. For example, the implant comprises a plurality of seeds. The implant can comprise an array, for example a planar array, of seeds. The seeds can be disposed in an array on the material, based on horizontal and vertical separation of the seeds. The implant can also comprise seeds arranged in a three dimensional construction. For example, the seeds can be disposed in a flexible mass (such as a sphere) of mesh that could be collapsed, inserted into a body cavity and allowed to naturally expand to fill the cavity. According to various embodiments, the mass could be flexible enough to conform to an area that would not be perfectly spherical. According to various embodiments, the mass could be expanded and/or compressed to a shape by natural stresses or forces.

According to various embodiments of the disclosure, the array can be provided pre-made, or standardized, with definite spacing between the seeds. This known array allows calculation of dosimetry to the treated area. The array could be constructed with a standard spacing, or be customized to a seed pattern desired by the end user. For example, the carrier could be provided without radioactive seeds and with provisions in the carrier, such as pouches or slits, to allow for loading of individual seeds by the end user. In this manner, the seeds can be disposed in the carrier with either standardized or customized spacing. A discrete seed spacing could be advantageous in that the end user would not have to weave a suture containing seeds into a mesh. This could provide a time savings, and could ensure that the seeds would have a definite spacing (independent of the skill of the end user in weaving a filament of seeds) and provide reproducible and calculable dosimetry.

According to various embodiments, the implant comprises a bioabsorbable or permanent carrier. Alternatively, the implant can comprise both bioabsorbable and permanent components in the carrier. The use of either a bioabsorbable or permanent carrier allows the physician to tailor the mechanical properties of the implant to fit the tumor type or location of the tumor/tumor bed.

There is a variety of radioactive seeds that can be used in accordance with the present disclosure. Suitable non-limiting examples of such seeds include, for example, $I^{125}$, $Pd^{103}$, $Cs^{131}$, $Au^{198}$, $Co^{60}$, and $Ir^{192}$. Those of ordinary skill in the art will appreciate that any seed or radioactive particle capable of providing a therapeutic dose of radiation can be used. Seeds can be made of a number of different materials known to the ordinary practitioner. For example, the seeds can be in the form of a metallic capsule, a polymer, a ceramic, a ribbon, or can be particulate in nature. Any form capable of providing the desired dose of radiation can be used.

The implant can comprise a variety of materials (in addition to the seeds). For example, the seeds can be entrained within a non-absorbable mesh. Suitable non-absorbable meshes are well-known, and include those disclosed in, for example, U.S. Pat. No. 6,971,252 (the disclosure of which is incorporated by reference herein). The meshes can be constructed of at least one of polypropylene, polyester, stainless steel, titanium, carbon fiber, nitinol, and other materials. According to various embodiments, the seeds can be entrained in a non-absorbable material, such as a non-absorbable polymeric sheet. Suitable non-limiting examples of polymeric sheets include polyurethane and silicone.

According to various embodiments, the seeds can be entrained within an absorbable mesh or sheet. Absorbable materials are well-known to those of ordinary skill in the art, and can be constructed of, for example, polydioxanone, polylactide, polyglycolic acid, and collagen, etc.

The seeds can be disposed in the carrier via a number of different mechanisms. For example, the seeds can be attached to the carrier via adhesives, welding, sewing, entrainment between two sheets of material, or placement into formed pockets on the material. The entrainment between two sheets of material can be accomplished by heat staking around the seeds to affix the two sheets together. The heat staking technique could be advantageous in that a second chemical and/or material would not necessarily need to be added to affix the seeds, and the tedious task of sewing with radioactive materials could be avoided. The original properties of the entrainment material, most importantly the ability of tissue to grow into the pores of the material, could also be maintained with minimal disruption during the staking process.

According to various embodiments, the carrier materials can be homogeneous, or can be constructed of layers or areas of dissimilar materials (e.g., a polypropylene mesh welded to a polyester mesh, with the seeds trapped between). This construction can be used to adjust physical and performance qualities, including but not limited to flexibility, degree of tissue in-growth, tensile or flexural strength, avenues for sterilization or processing, degree of seed retention, visibility by medical imaging modalities, attachment method to tissue or bone, degradation time, and control of tissue erosion.

The carrier material can incorporate additional elements for a variety of purposes. Suitable non-limiting examples of such elements include fiducial markers for visualization/localizing by medical imaging modalities (ultrasound, fluoroscopy, MRI, CT, etc.); visual markings indicating alignment, seed placement, seed placement distances, and/or tissue attachment points; and coatings to increase/reduce adhesion, promote/retard in-growth, cause coagulation of blood, provide tumoricidal activity, increase biocompatibility, reduce microbiological growth, etc. In addition, the carrier material can have incorporated therein, or attached thereon, features to ease attachment to tissue such as, for example, loops, arms, filaments, sutures, and staples.

According to various embodiments, the implant can comprise a radiation shielding backing material to afford a directional radiation dose. Suitable non-limiting examples of such materials include bismuth- or barium-loaded polymers. This backing material can be in the form of a solid sheet, or have open areas to allow selective dose transmission. Such a backing material could be useful to direct the dose towards areas of interest while shielding healthy or sensitive tissues or organs.

The above-described features of the various embodiments of the present method and apparatus are depicted in FIGS. 1-7.

FIG. 1, according to various embodiments, is an illustration of an implant in accordance with the present disclosure. In this embodiment a first sheet of material 101 may be operatively coupled to a second sheet of material 102. The second sheet of material 102 may have formed pockets 103 which hold seeds 104. The first and second sheets of material 101, 102 may be adhered to one another by heat staking around the seeds in areas 105.

Figure 2:
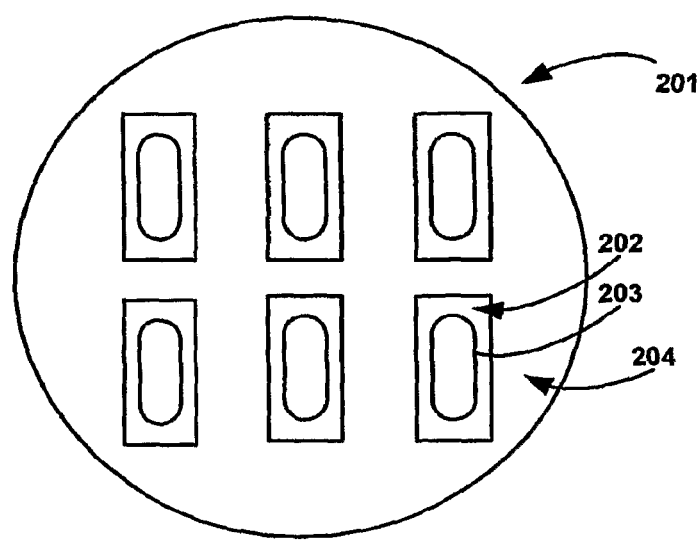
FIG. 2, according to various embodiments, is a detailed illustration of an implant having radioactive seeds in accordance with the present disclosure.

FIG. 2, according to various embodiments, is a detailed illustration of an implant 201 having radioactive seeds 203 in accordance with the present disclosure. The seeds 203 may be held in pockets 202 by staking areas 204. In this embodiment each pocket 202 may be surrounded by one common staking area 204.

Figure 3:
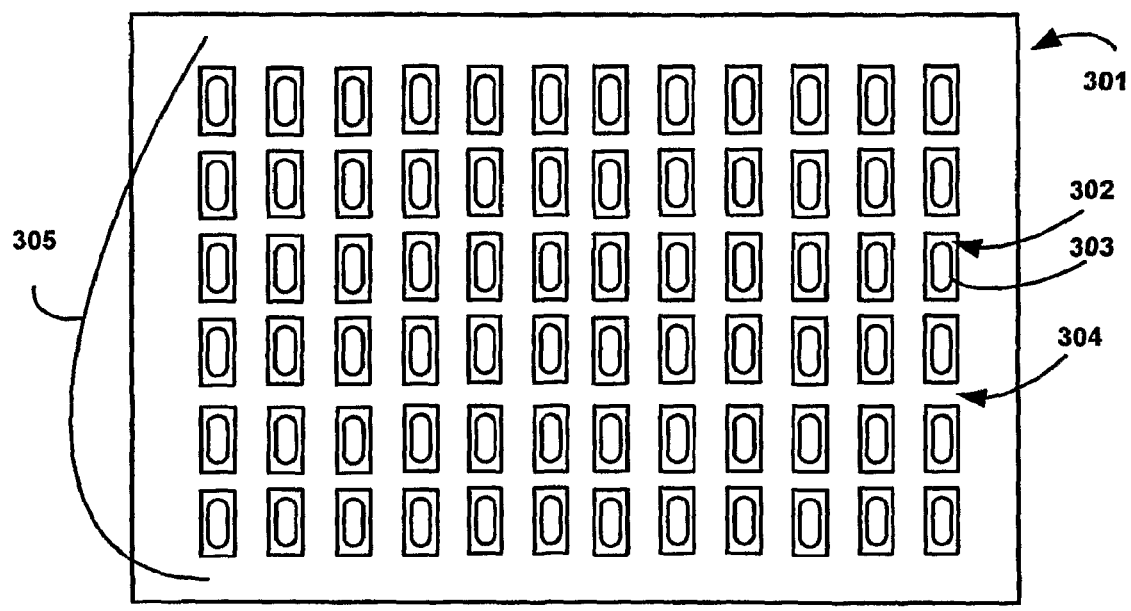
FIG. 3, according to various embodiments, is an overall illustration of an implant having radioactive seeds in accordance with the present disclosure.

FIG. 3, according to various embodiments, is an overall illustration of an implant 301 having radioactive seeds 303 in accordance with the present disclosure. The seeds 303 may be held in pockets 302 by staking area 304. The seeds 303 in the pockets 302 may be arranged in a predetermined pattern 305. The pattern 305 may be constructed with a standard spacing as depicted, or may be customized to a seed pattern desired by the end user.

Figure 4:
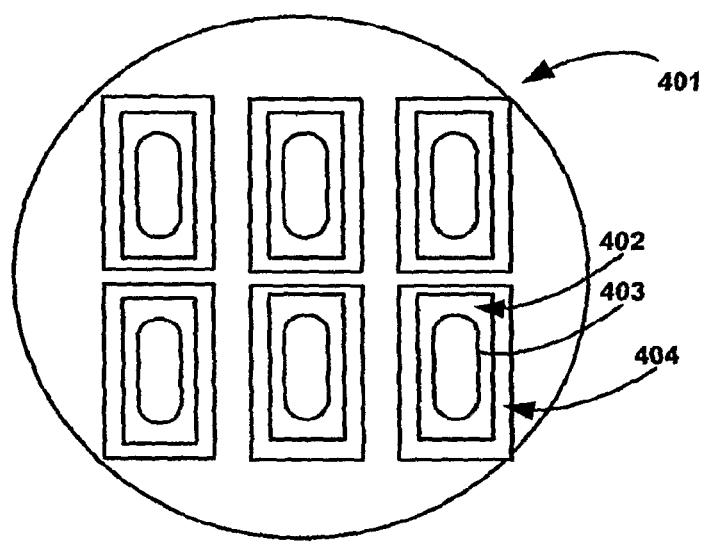
FIG. 4, according to various embodiments, is a detailed illustration of an alternative embodiment of an implant having radioactive seeds in accordance with the present disclosure.

FIG. 4, according to various embodiments, is a detailed illustration of an alternative embodiment of an implant 401 having radioactive seeds 403 in accordance with the present disclosure. The seeds 403 may be held in pockets 402 by staking areas 404. In this embodiment each pocket 402 is surrounded by its own respective staking area 404.

Figure 5:
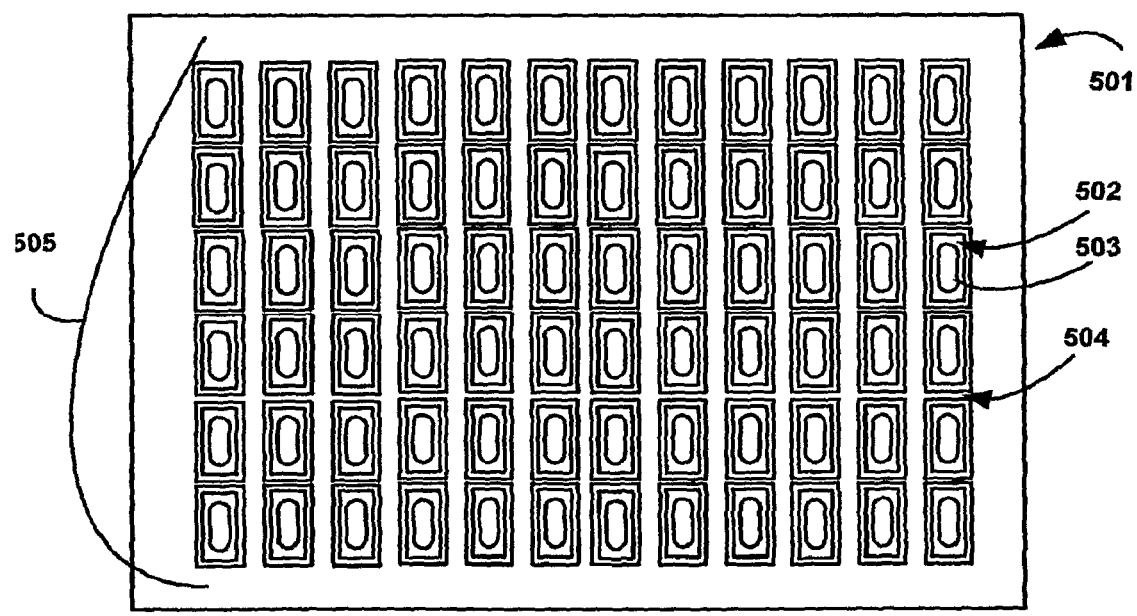
FIG. 5, according to various embodiments, is an overall illustration of an alternative embodiment of an implant having radioactive seeds in accordance with the present disclosure.

FIG. 5, according to various embodiments, is an overall illustration of an alternative embodiment of an implant 501 having radioactive seeds 503 in accordance with the present disclosure. The seeds 503 may be held in pockets 502 by individual staking areas 504. The seeds 503 in the pockets 502 may be arranged in a predetermined pattern 505. The pattern 505 may be constructed with a standard spacing as depicted, or may be customized to a seed pattern desired by the end user.

Figure 6:
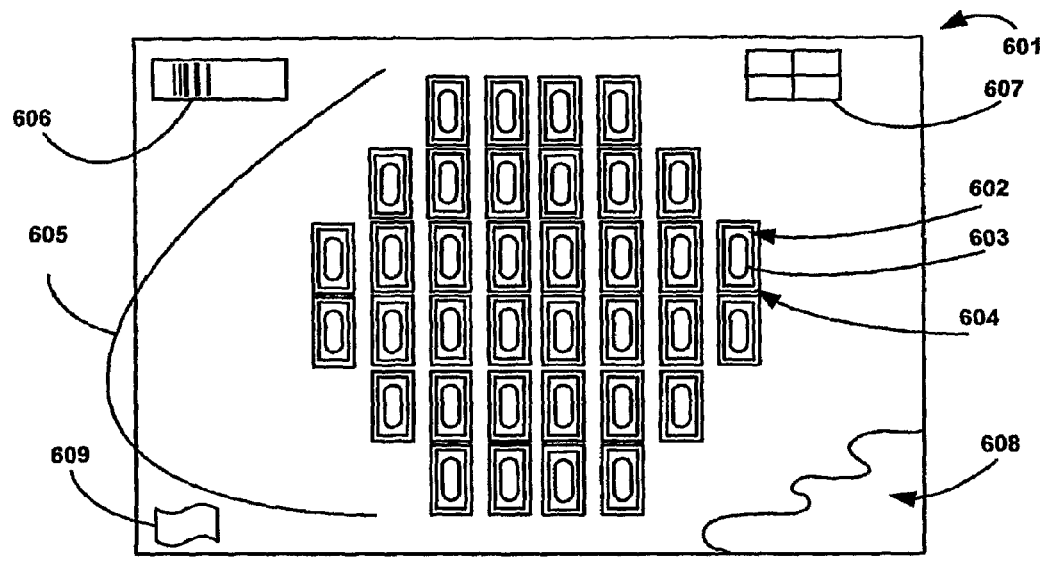
FIG. 6, according to various embodiments, is an overall illustration of an implant having radioactive seeds in a predetermined pattern in accordance with the present disclosure.

FIG. 6, according to various embodiments, is an overall illustration of an implant 601 having radioactive seeds 603 in a predetermined pattern 605 in accordance with the present disclosure. The seeds 603 may be held in pockets 602 by individual staking areas 604. The implant 601 may incorporate additional elements for a variety of purposes, such as, fiducial markers 606, visual markings 607, coatings 608, and attachment elements 609.

Figure 7:
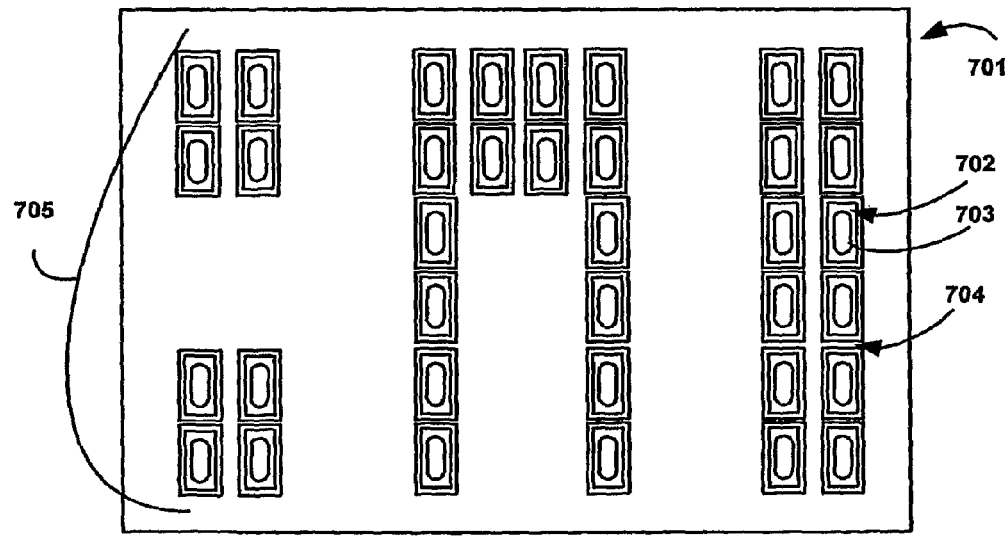
FIG. 7, according to various embodiments, is an overall illustration of an implant having radioactive seeds in another predetermined pattern in accordance with the present disclosure.

FIG. 7, according to various embodiments, is an overall illustration of an implant 701 having radioactive seeds 703 in another predetermined pattern 705 in accordance with the present disclosure. The seeds 703 may be held in pockets 702 by individual staking areas 704.

The implants can be attached to tissue using a variety of different methods. For example, the implants can be affixed to tissue via at least one of sutures, staples, tacks, adhesives, physical entrapment (chevrons), or other standard tissue-anchoring means. The implants can be permanently flexible, or can be rigid and formed into particular rigid shapes using heat and/or pressure based on the particular application. The implants could be constructed of materials that would change physical properties when contacted with body fluids or exposed to body temperature.

According to various embodiments, the implants can be applied externally or internally. For example, the implants can be inserted laparoscopically or by open surgery. The implants can be used in the body, or externally (i.e., a skin patch). The implant can be inserted into a tumor bed. For example, a tumor can be excised from a body cavity and the implant can be fixed to the locus thereof. The implant can be fixed to the tumor bed by a variety of different methods, including suturing, stapling, and adhesion. In the case of a spherical or semispherical implant, the implant can be inserted into the cavity and permitted to expand, thereby filling at least a portion of the cavity.

According to various embodiments, the implant can be provided simultaneously or sequentially with an adjunctive therapy. For example, the implant can comprise a slow-release chemotherapeutic agent. Such agents and their release profiles are well-known to those of ordinary skill in the art of, inter alia, oncology. In addition, external beam radiation can be provided as an adjunct to seed radiation.

For the purposes of this specification and appended claims, unless otherwise indicated, all numbers used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a mesh" includes two or more meshes.

Other various embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An implant comprising:
   at least two sheets of a biocompatible material;
   at least two radioactive seeds disposed between said sheets of biocompatible material,
   where the at least two radioactive seeds are disposed within a pocket formed in at least one of the two sheets of biocompatible material, wherein the seeds are disposed so as to be customized to a seed pattern desired by an end user; and
   a radiation shielding backing material configured to afford a directional radiation dose, wherein the backing material comprises open areas configured to allow selective dose transmission.

2. The implant according to claim 1, wherein the at least two radioactive seeds are at least substantially fixed into a position by at least one of the two sheets of biocompatible material.

3. The implant according to claim 1, wherein the at least two sheets of biocompatible material are bonded together at a perimeter around said at least two radioactive seeds.

4. The implant according to claim 1, wherein each of the at least two radioactive seeds are held in the pocket by a staking area.

5. The implant according to claim 1, wherein at least a portion of the biocompatible material is a bioabsorbable material.

6. The implant according to claim 1, wherein the at least two radioactive seeds are entrained in at least one of polypropylene, polyester, polyurethane, polydioxanone, polylactide, polyglycolic acid, collagen, silicon, stainless steel, titanium, carbon fiber, and nitinol.

7. The implant according to claim 1, wherein the at least two sheets of biocompatible material are bonded together at a perimeter around the at least two radioactive seeds by the application of heat.

8. The implant according to claim 1, wherein the biocompatible material comprises at least one of a fiducial marker, a visual marker, a coating, and an attachment feature.

9. The implant according to claim 1, wherein at least one of the at least two sheets of a biocompatible material comprises a radiation-shielding material.

10. The implant according to claim 9, wherein the radiation-shielding material is a polymeric material containing at least one of bismuth and barium.

11. The implant according to claim 1, wherein at least one of the sheets of the biocompatible material is an open-knit mesh that is coated with at least one biological material.

12. The implant according to claim 1, the pocket comprises one seed and the pocket is encircled by a staking area.

13. The implant according to claim 1, wherein the at least two radioactive seeds are disposed in a planar array.

14. The implant according to claim 1, wherein the at least two radioactive seeds are disposed in a three-dimensional array in the sheets of biocompatible material.

15. A method for treating a patient, comprising fixing to the tissue of the patient at least one implant according to claim 1.

16. The method according to claim 15, further comprising treating the patient with at least one additional therapy.

17. The method according to claim 16, wherein the at least one additional therapy is chosen from chemotherapy and external beam radiation.

18. The method according to claim 15, wherein said implant is fixed to the tissue by at least one of sutures, staples, tacks, adhesives, and chevrons.

19. The method according to claim 15, wherein the implant is laparoscopically inserted into the patient.

20. A method for treating a patient, comprising surgically excising at least a portion of a tumor from surrounding tissue, and providing at least one implant according to claim 1 at the locus of said surrounding tissue.

21. The method according to claim 20, wherein the implant is provided laparoscopically to the patient.

22. A method for irradiating a tumor bed, comprising providing an implant according to claim 1 sufficiently proximate to the tumor bed to irradiate said tumor.

23. The method according to claim 22, wherein the implant is fixed to the wall of the tumor bed.

24. An apparatus, comprising:
  first and second sheets of material operatively coupled to one another in at least one attachment area,
  at least one of the first and second sheets of material having a plurality of formed pockets arranged in a predetermined pattern;
  a plurality of radioactive seeds arranged respectively in the plurality of formed pockets, wherein the seeds are disposed so as to be customized to a seed pattern desired by an end user; and
  a radiation shielding backing material configured to afford a directional radiation dose,
  wherein the backing material comprises open areas configured to allow selective dose transmission.

25. The apparatus according to claim 24, wherein at least one of the first and second sheets of material comprises a radiation shielding backing material to afford a directional radiation dose.

26. The apparatus according to claim 24, wherein the first and second sheets of material are coupled by heat staking around the plurality of seeds to form the plurality of pockets.

27. The apparatus according to claim 26, wherein the heat staking forms a contiguous staking area encircling a radioactive seed.

28. The apparatus according to claim 26, wherein the heat staking forms a plurality of staking areas, a respective staking area being associated with a respective pocket of the plurality of pockets where the respective pocket holds a radioactive seed.

29. The apparatus according to claim 24, wherein the first and second sheets of material are formed of biocompatible material.

30. The apparatus according to claim 24, wherein the first and second sheets are formed of a biocompatible material and are bonded together at respective perimeters to encircle the radioactive seeds.

31. The apparatus according to claim 30, wherein the first and second sheets are formed of biocompatible material that is a bioabsorbable material.

32. The apparatus according to claim 24, wherein the apparatus further comprises at least one of a fiducial marker, a visual marker, a coating, and an attachment element on at least one of the first and second sheets of material.

33. The apparatus according to claim 24, wherein at least one of the first and second sheets are formed of a biocompatible material that comprises a radiation-shielding material.

34. The apparatus according to claim 24, wherein at least one of the first and second sheets are formed of a biocompatible material that is an open-knit mesh.

35. A method, comprising:
  forming a plurality of pockets in a predetermined pattern in at least one of first and second sheets of material;
  inserting a plurality of radioactive seeds corresponding to the plurality of formed pockets;
  coupling at least one of the first and second sheets of material to a radiation shielding backing material configured to afford a directional radiation dose; and
  coupling the first and second sheets of material to one another in at least one attachment area, wherein the inserting step comprises disposing the seeds so as to be customized to a seed pattern desired by an end user, wherein the backing material comprises open areas configured to allow selective dose transmission.

36. The method according to claim 35, wherein at least one of the first and second sheets of material comprises a radiation shielding backing material to afford a directional radiation dose.

37. The method according to claim 35, wherein the first and second sheets of material are coupled by heat staking around the plurality of seeds to form the plurality of pockets such that each pocket holds a radioactive seed.

38. The method according to claim 37, wherein the heat staking forms a contiguous staking area encircling a radioactive seed.

39. The method according to claim 37, wherein the heat staking forms a plurality of staking areas, a respective staking area being associated with a respective pocket of the plurality of pockets.

* * * * *